United States Patent
Day et al.

(10) Patent No.: US 12,076,427 B2
(45) Date of Patent: *Sep. 3, 2024

(54) COMPOSITIONS HAVING LOW SULFATE CONTAINING SURFACTANTS

(71) Applicant: Conopco, Inc., Englewood Cliffs, NJ (US)

(72) Inventors: Kimberly Day, Orange, CT (US); Morgan Nicole Kozar, Milford, CT (US); Matthew Joseph Rienzo, Fairfield, CT (US); Tirucherai Varahan Vasudevan, Bethany, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/881,901

(22) Filed: Aug. 5, 2022

(65) Prior Publication Data

US 2023/0000743 A1   Jan. 5, 2023

Related U.S. Application Data

(63) Continuation of application No. 16/832,644, filed on Mar. 27, 2020, now Pat. No. 11,523,978.

(51) Int. Cl.
| | | |
|---|---|---|
| A61K 8/00 | (2006.01) | |
| A61K 8/34 | (2006.01) | |
| A61K 8/368 | (2006.01) | |
| A61K 8/44 | (2006.01) | |
| A61K 8/46 | (2006.01) | |
| A61Q 19/10 | (2006.01) | |

(52) U.S. Cl.
CPC .............. *A61K 8/368* (2013.01); *A61K 8/345* (2013.01); *A61K 8/44* (2013.01); *A61K 8/442* (2013.01); *A61K 8/46* (2013.01); *A61K 8/463* (2013.01); *A61K 8/466* (2013.01); *A61Q 19/10* (2013.01); *A61K 2800/524* (2013.01); *A61K 2800/596* (2013.01); *A61K 2800/87* (2013.01)

(58) Field of Classification Search
CPC .................................................... A61K 8/368
See application file for complete search history.

(56) References Cited

U.S. PATENT DOCUMENTS

| | | |
|---|---|---|
| 398,418 A | 2/1889 | Linn |
| 5,009,814 A | 4/1991 | Kelkenberg et al. |
| 5,389,279 A | 2/1995 | Au et al. |
| 5,393,466 A | 2/1995 | Ilardi et al. |
| 5,872,111 A | 2/1999 | Au et al. |
| 6,294,186 B1 | 9/2001 | Beerse et al. |
| 7,582,681 B2 | 9/2009 | Schmaus et al. |
| 10,357,442 B2 | 7/2019 | Schelges et al. |
| 2005/0266034 A1* | 12/2005 | Muller ............ A61K 8/44 424/401 |
| 2012/0019744 A1 | 1/2012 | Lee |
| 2016/0000669 A1 | 1/2016 | Hinman et al. |
| 2016/0053206 A1 | 2/2016 | Chandar et al. |
| 2018/0193243 A1 | 7/2018 | Koshti et al. |
| 2022/0145050 A1* | 5/2022 | McAlpin ............ C08J 11/04 |

FOREIGN PATENT DOCUMENTS

| | | |
|---|---|---|
| DE | 102015225004 | 6/2017 |
| DE | 102018214573 | 3/2020 |
| EP | 1964541 | 9/2008 |
| EP | 2409680 | 6/2015 |

OTHER PUBLICATIONS

Mintel; Nourishing Body Wash; Dove Sensitive Skin Body Wash; Nov. 2015; 1-3.
Search Report and Written Opinion in EP20169711; Sep. 3, 2020.
Iselux LQ-CLR-SB-Sodium Lauroyl Methyl Isethionate; Innospecinc.com; 2010; pp. 1-2.
Search Report and Written Opinion in PCTEP2021057380; Jul. 14, 2021.

* cited by examiner

*Primary Examiner* — Necholus Ogden, Jr.
(74) *Attorney, Agent, or Firm* — Edward A. Squillante, Jr.

(57) ABSTRACT

The invention is directed to a composition suitable for topical application that comprises a naturally derived preservative having benzoic acid or a derivative thereof. The composition is stable when preserved with the naturally derived preservative and when at a pH that is above the natural pH of skin to as high as 7.25.

25 Claims, No Drawings

COMPOSITIONS HAVING LOW SULFATE CONTAINING SURFACTANTS

FIELD OF THE INVENTION

The present invention is directed to a composition comprising a naturally derived preservative. More particularly, the invention is directed to a composition having a pH that is over the natural pH of skin and that comprises a specific zwitterionic to anionic surfactant system. The composition is, unexpectedly, preserved with a naturally derived preservative comprising benzoic acid and/or a derivative thereof. The preservative surprisingly provides superior antimicrobial benefits to compositions having a surfactant system with zwitterionic to anionic surfactant at a weight ratio of 1:8 to 1:2, even when such compositions are formulated to have a pH over the natural pH of skin to as high as 7.25 and less than 8.0% by weight total sulfate-based surfactant. In addition to having antimicrobial stability, the compositions of the present invention are mild, remain free of discoloration, syneresis and odor after being stored for 3 months at 45° C.

BACKGROUND OF THE INVENTION

DMDM hydantoin, parabens, methylisothiazolinone as well as methylchloroisothiazolinone are commonly used preservatives found in consumer products. Such preservatives have been safely used for years and are known to work well at maintaining the integrity and stability of certain end use compositions. Another preservative suitable for use in consumer products is sodium benzoate. However, sodium benzoate, while generally regarded as safe, is well known for use in compositions that are well within an acidic pH range and under the natural pH of skin. Notwithstanding, there is a desire to use naturally derived preservatives, and especially, preservatives that include components suitable to work well across a full range of consumer products that are formulated at a pH that is over the natural pH of skin. Moreover, such naturally derived preservatives should be effective at preserving products, not be skin sensitizing and not negatively impact the sensorial characteristics of consumer products they are formulated in, and particularly, those that are topically applied. They should also not induce any negative composition characteristics, like color change, odor or syneresis to the products they are added to.

In addition to delivering superior antimicrobial benefits, the naturally derived preservative should not be harmful to the environment and gentle enough for use on the most fragile consumer, babies.

This invention, therefore, is directed to a composition having a specific surfactant ratio and a naturally derived preservative. The preservative comprises benzoic acid and/or a derivative thereof that, surprisingly, provides superior antimicrobial benefits to compositions having a weight ratio of zwitterionic to anionic surfactant from 1:8 to 1:2, even when such compositions are formulated to have a pH over the natural pH of skin to as high as 7.25 and less than 8.0% by weight sulfate-based surfactant. Moreover, such a preservative system unexpectedly does not negatively impact the composition's stability, color and odor, and provides superior antimicrobial benefits when formulated therein.

ADDITIONAL INFORMATION

Efforts have been disclosed for making preservative systems. In U.S. Published Patent Application 2012/0190744A1, preservative systems for cosmetic formulations are disclosed.

Still other efforts have been disclosed for making preservative systems. In U.S. Patent Application No. US 2018/0193243 A1, non-toxic preservative compositions are disclosed.

Even other efforts have been disclosed for making synergistic mixtures. In U.S. Pat. No. 7,582,681B2, antimicrobial active compounds with 1,2-alkane diols are disclosed.

Yet other efforts have been described for making personal wash compositions. In U.S. Pat. No. 5,872,111, compositions comprising glycosylamide surfactants are described.

None of the additional information above describes a composition having a naturally derived preservative system and zwitterionic and anionic surfactant at a weight ratio from 1:8 to 1:2 as described and claimed in the present invention.

SUMMARY OF THE INVENTION

In a first aspect, the present invention is directed to a composition comprising:
  (a) preservative comprising benzoic acid and/or a derivative thereof
  (b) an anionic surfactant comprising an alkyl sulfate, alkyl ether sulfate or mixture thereof, and an isethionate, taurate, glycinate or a mixture thereof;
  (c) a zwitterionic surfactant comprising a betaine, a sultaine or a mixture thereof;
  (d) 1 to 9% by weight of a polyol; and
  (e) water,
the composition having a water activity under 1, a pH from 5.75 to 7.25, over 5.0% by weight total surfactant and a weight ratio of zwitterionic surfactant to anionic surfactant that is from 1:8 to 1:2 wherein the isethionate is at least 50% by weight of a lauroyl isethionate and the composition comprises less than 8.0% by weight sulfate-based surfactant.

In a second aspect, the present invention is directed to a method for treating skin, cosmetically, by contacting the skin with the composition of the first aspect of the invention.

All other aspects of the present invention will more readily become apparent from the description and examples which follow.

Skin, as used herein, is meant to include skin on the arms (including underarms), face, feet, neck, chest, hands, legs, buttocks and scalp (including hair). Naturally derived preservative, as used herein, means a preservative that can be naturally derived and that comprises benzoic acid and/or a derivative thereof. For the avoidance of doubt, preservatives that comprise benzoic acid and/or derivatives thereof can be synthetically made and they also are suitable for use in the compositions of this invention at the identified pH values. Composition, as used herein, is meant be an end use composition including a composition ready for topical application such as a cream, lotion, balm, serum, gel, mousse, aerosol, deodorant, antiperspirant, shampoo, conditioner, make-up or personal wash, including bars and liquids. Such a composition may also be a home care composition such as a hard surface cleaner or laundry detergent composition. In one embodiment, the composition is a liquid personal wash composition, and most preferably, a liquid body wash. In another embodiment, the composition is a shampoo composition. As hereinafter described, the composition of the present invention may optionally comprise skin benefit ingredients added thereto such as emollients, vitamins and/or derivatives thereof, resorcinols, retinoic acid precursors, colorants, moisturizers, sunscreens, mixtures thereof or the like. The skin benefit ingredients may be water or oil soluble. The composition, therefore, is an aqueous based composition with a pH from 5.75 to 7.25, and the composition can be water or oil continuous but is preferably water continuous. Sulfate-based means having an SO₄ group such as the one in sodium lauryl sulfate whereby mild surfactant system means less than 8.0% by weight sulfate-based surfactant. Viscosity, as used herein, is taken with a Brookfield RV5 suitable for isotropic compositions, at 20 rpm for 30 seconds and at 25° C. In still another embodiment, the composition of this invention is a non-therapeutic and cosmetic composition which is a liquid personal wash, leave-on skin lotion or cream. In the absence of explicitly stating otherwise, all ranges described herein are meant to include all ranges subsumed therein. Color stability means no negative and discernible color change such as a white to brown color change as observed by trained panelists. Superior antimicrobial benefits means at least a 3 log bacteria and kill at 7 days and at least a 2 log yeast and mold kill at 7 days, all as described in General Chapter 51 of the United States Pharmacopeia (USP). The term comprising is meant to encompass the terms consisting essentially of and consisting of. For the avoidance of doubt, and for illustration, a composition of this invention comprising an anionic and zwitterionic surfactant, water, sodium benzoate and polyol is meant to include a composition consisting essentially of the same and a composition consisting of the same. Except in the operating comparative examples, or where otherwise explicitly indicated, all numbers in this description indicating amounts or ratios of materials or conditions and/or physical properties of materials and/or use are to be understood as modified by the word "about". In a most preferred embodiment of the invention, the composition of this invention is a body wash composition having a viscosity from 750 to 22,000 cps, including all ranges subsumed therein.

DETAILED DESCRIPTION OF THE PREFERRED EMBODIMENTS

As to the naturally derived preservative suitable for use in the present invention, the same comprises benzoic acid and/or a derivative thereof. In an embodiment of the invention, the naturally derived preservative is from 80 to 100% by weight benzoic acid, a benzoic acid derivative or mixture thereof based on total weight of the preservative used in the composition ready for consumer use. In an optional embodiment of the invention, an additional naturally derived preservative may be used with the benzoic acid and/or derivative thereof. The only limitation with respect to the additional naturally derived preservative that may be used is that the same is suitable for use in a composition that is being used by consumers, and especially used, for topical application. Illustrative examples of the additional yet optional naturally derived preservative that may be used in the present invention includes gluconolactone, calcium gluconate, glucuronic acid lactone, thymol, magnolol extract, biopein, suprapein, neopein, sorbic acid, citric acid, rosemary extract, potassium sorbate mixtures thereof or the like. In a preferred embodiment, the naturally derived preservative used in the present invention is 90 to 100% by weight benzoic acid, benzoic acid derivative or mixture thereof based on total weight of the preservative used. In a most preferred embodiment, the naturally derived preservative used in the present invention is 95 to 100% by weight benzoic acid, benzoic acid derivative or mixture thereof based on total weight of the preservative used. In still another embodiment of the invention, the naturally derived preservative used in the present invention is all (100% by weight) benzoic acid, benzoic acid derivative or a mixture thereof based on total weight of preservative used. In still yet another preferred embodiment, the naturally derived preservative used in the present invention (i.e., benzoic acid derivative) is sodium benzoate, potassium benzoate, amino benzoate or a mixture thereof. When used, the preferred amino benzoate employed in the composition of the present invention is sodium or potassium p-amino benzoate or a mixture thereof. In yet another preferred embodiment, the naturally derived preservative used in the present invention is sodium benzoate.

Regarding the amount of naturally derived preservative used in the present invention, typically the same makes up from 0.20 to 2.0%, and preferably, from 0.3 to 1.5%, and most preferably, from 0.35 to 1.5% by weight of the composition, including all ranges subsumed therein. In still another embodiment, the naturally derived preservative makes up from 0.4 to 0.65% by weight of the composition, including all ranges subsumed therein.

The anionic surfactant suitable for use in the present invention comprises an alkyl sulfate, alkyl ether sulfate or mixtures thereof. The alkyl sulfate (e.g., $C_{12}$-$C_{18}$ alkyl sulfate) suitable for use includes sodium, potassium, ammonium or substituted ammonium salts of laury sulfate, pareth sulfate, myreth sulfate, stearyl sulfate, capric sulfate or a mixture thereof. As to the alkyl ether sulfate suitable for use in the present invention (including alkyl glyceryl ether sulfates), these include surfactants having the formula:

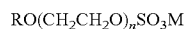

$$RO(CH_2CH_2O)_nSO_3M$$

wherein R is an alkyl or alkenyl having 8 to 18 carbons, preferably 12 to 18 carbons, n has an average value of at least 1, preferably less than 5, and most preferably 1 to 4, and M is a solubilizing cation such as sodium, potassium, ammonium or substituted ammonium. Regarding the anionic sulfate-based surfactant used in this invention (i.e., not isethionate, taurate and/or glycinate), the preferred alkyl ether sulfate suitable for use is sodium lauryl ether sulfate, and the preferred alkyl sulfate is sodium lauryl sulfate. Mixtures of sodium lauryl ether sulfate and sodium lauryl sulfate may also be used. In an embodiment of the invention, the sulfate based surfactant used is at least 35%, and preferably, at least 40%, and most preferably, from 45 to 95% by weight sodium lauryl ether sulfate, based on total weight of sodium lauryl ether sulfate and sodium lauryl sulfate that make up the sulfate-based surfactant used in the composition. The sodium lauryl ether sulfate used in the invention can have 1, 2, 2.5, 3, 4, 5, or 6 poly(ethylene oxide) units (e.g., EO units) or a mixture thereof. In an often preferred embodiment, the sodium lauryl ether sulfate used is a mixture of surfactants with 1, 2 and 3 EO units. Such a mixture will typically have from 10 to 90% by weight sodium lauryl ether sulfate based on total weight of the mixture. In still another preferred embodiment, the mixture has between 45 to 65% by weight sodium lauryl ether sulfate and from 35 to 55% by weight sodium lauryl sulfate, based on total amount of sulfate-based surfactant in the composition and including all ranges subsumed therein.

The isethionate (i.e., additional anionic surfactant) suitable for use in the present invention along with the sulfate comprising surfactant will comprise at least 50% by weight of a lauroyl isethionate. Additional acyl isethionates that may be used with a lauroyl isethionate will include those (like lauroyl isethionate) that are generally classified as $C_8$-$C_{18}$ acyl isethionates. The isethionate surfactants suitable for use in this invention are prepared by a reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates suitable for use may also include alkoxylated isethionates such as those described in Ilardi et al., U.S. Pat. No. 5,393,466, entitled "Fatty Acid Esters of Polyalkoxylated isethionic acid; issued Feb. 28, 1995; incorporated herein by reference.

Such surfactants have the general formula:

$$R^1C-O(O)-C(X)H-C(Y)H_2-(OCH-COH_2)_m-SO_3M$$

wherein $R^1$ is an alkyl group having 8 to 18 carbons, m is an integer from 1 to 4, X and Y are each independently hydrogen or an alkyl group having 1 to 4 carbons and M is a solubilizing cation as previously described. In a preferred embodiment of the present invention, the isethionate used in addition to lauroyl isethionate is a cocoyl isethionate, lauroyl methyl isethionate or a mixture thereof whereby such isethionates are solubilized with a cation which is typically sodium, potassium, ammonium or substituted ammonium. In an embodiment of the invention, at least 75% by weight of the total weight of isethionate used in the invention is sodium lauroyl isethionate. In yet another embodiment, at least 85% by weight, and preferably, at least 95% by weight of the total weight of isethionate used in the composition of the invention is sodium lauroyl isethionate. In still another embodiment of the invention, all (100%) of the isethionate used in the present invention is sodium lauroyl isethionate.

As to the taurates that may be used, these include acyl taurates, including methyl acyl taurates. Often, the taurates that may be used in the present invention include those generally identified by the formula:

$$R^5CONR^6CH_2CH_2SO_3M$$

wherein $R^5$ is a $C_8$-$C_{20}$ alkyl, $R^6$ is a $C_1$-$C_4$ alkyl.
M is a solubilizing cation as previously described.

In an embodiment of the invention, when a taurate is used sodium methyl lauroyl taurate, sodium methyl cocoyl taurate or a mixture thereof is generally preferred.

As to glycinates suitable for use, these include acyl glycinates like sodium lauroyl glycinate, sodium cocoyl glycinate or a mixture thereof.

Typically, anionic surfactant makes up from 4 to 15%, and preferably, from 5 to 12%, and most preferably, from 6 to 10% by weight of the composition (e.g., end use liquid personal wash composition), including all ranges subsumed therein with the proviso that the total weight of anionic surfactant which is sulfate-based is less than 8.0%, and preferably, less than 7.5%, and most preferably, less than 7.2% by weight based on total weight of the composition. In an often-desired embodiment, sulfate-based surfactant makes up at least 4.0% by weight of the total weight of the composition. The isethionate which is at least 50% by weight sodium lauroyl isethionate based on total amount of isethionate used in the composition typically makes up from 0.4 to 4%, and preferably, from 0.5 to 2%, and most preferably, from 0.75 to 1.5% by weight of the composition.

As to the zwitterionic surfactant used in the present invention and comprising a betaine, sultaine or mixture thereof, the same include simple betaines of formula:

$$R^2-N^+-(R^3)(R^4)CH_2CO_2^-$$

and amido betaines of formula:

$$R^2-CONH(CH_2)_t-N^+-(R^3)(R^4)CH_2CO_2^- \text{ where t is 2 or 3.}$$

In both formulae, independently, $R^2$ is alkyl or alkenyl of 7 to 18 carbon atoms; $R^3$ and $R^4$ are each independently alkyl, hydroxyalkyl or carboxyalkyl of 1 to 3 carbon atoms; $R^2$ may, in particular, be a mixture of $C_{12}$ and $C_{14}$ alkyl groups derived from coconut oil so that at least half, preferably at least three quarters of the groups $R^2$ have 10 to 14 carbon atoms. $R^3$ and $R^4$ are preferably methyl.

A further possibility is that the zwitterionic surfactant is a sulphobetaine of the formula:

$$R^2-N^+-(R^3)(R^4)(CH_2)_3SO_3^-$$

or $$R^2-CONH(CH_2)_u-N^+-(R^3)(R^4)(CH_2)_3SO_3^-$$

where u is 2 or 3, or variants of these in which $-(CH_2)_3SO_3^-$ is replaced by $-CH_2C(OH)(H)CH_2SO_3^-$.

In these formulae, $R^2$, $R^3$ and $R^4$ are as previously defined.

Illustrative examples of the zwitterionic surfactants suitable for use include betaines like cocodimethyl carboxymethyl betaine, cocoamidopropyl betaine, laurylamidopropyl betaine or mixtures thereof. An additional zwitterionic surfactant suitable for use includes cocoamidopropyl sultaine. In an embodiment of the invention, the zwitterionic surfactant used is a betaine and at least 65% by weight, and preferably, at least 80% by weight, and most preferably, at least 95% by weight cocoamidopropyl betaine based on total weight of zwitterionic surfactant used. In an especially preferred embodiment of the invention, the zwitterionic surfactant used is all cocoamidopropyl betaine. Such zwitterionic surfactants are made commercially available from suppliers like Stepan Company.

The betaine used typically makes up from 0.8 to 7%, and preferably, from 1.0 to 5%, and most preferably, from 1.5 to 3.5% by weight of the composition. In even another preferred embodiment, betaine makes up from 2 to 3% by weight of the composition, including all ranges subsumed therein.

The weight ratio of zwitterionic to anionic surfactant in the present invention is 1:8 to 1:2, and preferably, from 1:6 to 1:2, and most preferably, from 1:5 to 1:3, including all weight ratios subsumed therein. In an embodiment of the invention, the weight ratio of zwitterionic to anionic surfactant is from 1:4 to 1:3, including all ranges subsumed therein.

The polyol suitable for use in the present invention is limited only to the extent that it is suitable for use in a topical composition and water soluble. Illustrative and nonlimiting examples of the polyols that may be used in the present invention include sorbitol, glycerol, mannitol, xylitol, maltitol or mixtures thereof. In an embodiment of the invention, the polyol used is at least 50% by weight glycerol, based on total weight of the polyol used in the composition. In another embodiment of the invention, the polyol used is all glycerol (100% by weight). Polyol will typically make up from 1.5 to 9% by weight of the composition, and preferably, from 2 to 8% by weight of the wash composition, and most preferably, from 2 to 7% by weight of the composition, including all ranges subsumed therein.

The composition of the present invention will comprise 40 to 90% by weight water, and more preferably, from 45 to 85% by weight water, and most preferably, from 50 to 80% by weight water. Such a composition will have a pH from 5.75 to 7.25, and preferably, from 6 to 7, and most preferably, from 6.2 to 6.8. In yet another embodiment of the invention, the pH of the composition is from 6.25 to 6.75.

The viscosity of the composition of the present invention is typically from 750 to 22,000 cps, and preferably, from 2,000 to 18,000 cps, and most preferably, from 5,000 to 16,000 cps. Such a composition is isotropic, and typically translucent or transparent. Water activity of the composition of this invention is typically under 1, preferably from 0.94 to 0.99, and most preferably, from 0.95 to 0.98 as measured with an Aqualab Activity Meter.

Oils may optionally be used in the compositions of the present invention. Oils suitable for use include silicone oils. Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, and preferably, from 4 to 5 silicon atoms. Nonvolatile silicone oils useful in this invention include polyalkyl siloxanes, polyalkylaryl siloxanes and polyether siloxane copolymers. Such essentially non-volatile polyalkyl siloxanes useful herein include, for example, polydimethylsiloxanes (like dimethicone) with viscosities of from 5 to 100,000 centistokes at 25° C. An often preferred silicone source is a cyclopentasiloxane and dimethicone solution.

Suitable esters for optional use in the composition with the naturally derived preservative of this invention include: (1) Alkenyl or alkyl esters of fatty acids having 10 to 20 carbon atoms like isopropyl palmitate, isopropyl isostearate, isononyl isonanonoate, oleyl myristate, isopropyl myristate, oleyl stearate, and oleyl oleate; (2) Ether-esters such as fatty acid esters of ethoxylated fatty alcohols; (3) Polyhydric alcohol esters such as ethylene glycol mono- and di-fatty acid esters, diethylene glycol mono- and di-fatty acid esters, polyethylene glycol (200-6000) mono and di-fatty acid esters, propylene glycol mono- and di-fatty acid esters, polypropylene glycol 2000 monooleate, polypropylene glycol 2000 mono stearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxy-ethylene sorbitan fatty acid esters; (4) Sterol esters, of which soya sterol and cholesterol fatty acid esters are examples thereof.

Still other oils that may be used include triglycerides (animal and/or vegetable) like soybean oil (including hydrogenated soybean oil), sunflower oil, coconut oil, palm kernel oil, castor oil, rapeseed oil, palm oil, grape seed oil, shea butter, caprylic/capric triglyceride, safflower oil, fish oil or mixtures thereof.

Even other oils suitable for use include mineral oil, jojoba oil, isoparaffins, $C_{12}$-$C_{15}$ alkyl benzoates, polyalphaolefins, isohexadecane, petrolatum, mixtures thereof (including with those oils above) or the like. Soybean and sunflower oil are often preferred triglyceride oils. Caprylic/capric triglyceride is another oil that may optionally be used in the composition of the present invention.

These optional oils suitable for use make up from 0 to 10% by weight of the composition. In an embodiment of the invention, petrolatum makes up from 0.01 to 6%, and preferably, from 0.5 to 5%, and most preferably, from 1.0 to 4.0% by weight of the composition, including all ranges subsumed therein.

Adjusters suitable to modify the pH of the compositions of this invention may be used. Such pH adjusters include triethylamine, NaOH, KOH, $H_2SO_4$, HCl, $C_6H_8O_7$ (i.e., citric acid) or mixtures thereof. The pH adjusters are added at amounts such that the final pH of the composition is as defined herein (e.g., from 5.75 to 7.25).

The pH of the composition is assessed by using conventional instrumentation such as a pH meter made commercially available from Thermo Scientific®.

In an embodiment of the invention, the composition of the present invention may include optional surfactants in addition to the anionic and zwitterionic surfactants herein described. When such surfactants are used in the composition of the present invention, they typically make up no more than 8% by weight of the composition. In an embodiment of the invention, when such additional surfactants are used, they typically make up from 0.0001 to 7% and preferably, from 0.001 to 5% by weight of the composition. Therefore, it is within the scope of the present invention to optionally include conventional soaps and/or syndets in the compositions of the present invention.

Optional surfactants that may be used include alkyl sulfosuccinates (including mono- and dialkyl, e.g., $C_6$-$C_{22}$ sulfosuccinates); alkyl and acyl sarcosinates, sulfoacetates, $C_8$-$C_{22}$ alkyl phosphates and phosphonates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

In an embodiment of the invention, additional optional surfactants can include sodium lauroyl glutamate, sodium cocoyl glutamate or a mixture thereof. Such anionic surfactants described herein are commercially available from suppliers like Galaxy Surfactants, Clariant, Sino Lion and Innospec.

Amphoteric surfactants that optionally may be used in the compositions (which depending on pH can be zwitterionic) of the present invention include sodium acyl amphoacetates, sodium acyl amphopropionates, disodium acyl amphodiacetates and disodium acyl amphodipropionates where the acyl (i.e., alkanoyl group) can comprise a $C_7$-$C_{18}$ alkyl portion. Illustrative examples of the amphoteric surfactants suitable for optional use include sodium lauroamphoacetate, sodium cocoamphoacetate, sodium lauroamphoacetate, sodium cocoamphoacetate and mixtures thereof.

Nonionic surfactants may optionally be used in the composition of the present invention. When used, nonionic surfactants are typically used at levels as low as 0.5, 1, 1.5 or 2% by weight and at levels as high as 4 or 6% by weight. The nonionics which may optionally be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic surfactant compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other nonionic surfactants include long chain tertiary amine oxides, long chain tertiary phosphine oxides, dialkyl sulphoxides, and the like.

In an embodiment of the invention nonionic surfactants that may optionally be used include fatty acid/alcohol ethoxylates having the following structures a) $HOCH_2(CH_2)_s(CH_2CH_2O)_v H$ or b) $HOOC(CH_2)_c(CH_2CH_2O)_d H$; where s and v are each independently an integer up to 18; and c and d are each independently an integer from 1 or greater. In an embodiment of the invention, s and v are each independently 6 to 18; c and d are each independently 1 to 30. Other options for nonionic surfactants include those having the formula $HOOC(CH_2)_i$—$CH$=$CH$—$(CH_2)_k$ $(CH_2CH_2O)_z$ H, where i, k are each independently 5 to 15; and z is 5 to 50. In another embodiment of the invention, i and k are each independently 6 to 12; and z is 15 to 35.

The optional nonionic may also include a sugar amide, such as a polysaccharide amide. Specifically, the surfactant may be one of the lactobionamides described in U.S. Pat. No. 5,389,279 to Au et al., entitled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic surfactants may optionally be used in the compositions of the present invention. One class of cationic surfactants suitable for optional use includes heterocyclic ammonium salts such as cetyl or stearyl pyridinium chloride, alkyl amidoethyl pyrrylinodium methyl sulfate, and lapyrium chloride.

Tetra alkyl ammonium salts are another useful optional class of cationic surfactants suitable for use. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides, and behenyl dimethyl ammonium chloride.

Still other types of cationic surfactants that may be used optionally are the various ethoxylated quaternary amines and ester quats. Examples include PEG-5 stearyl ammonium lactate (e.g., Genamin KSL manufactured by Clariant), PEG-2 coco ammonium chloride, PEG-15 hydrogenated tallow ammonium chloride, PEG 15 stearyl ammonium chloride, dipalmitoyl ethyl methyl ammonium chloride, dipalmitoyl hydroxyethyl methyl sulfate, and strearyl amidopropyl dimethylamine lactate.

Even other useful cationic surfactants suitable for optional use include quaternized hydrolysates of silk, wheat, and keratin proteins, and it is within the scope of the invention to use mixtures of the aforementioned cationic surfactants.

Unlike the other optional surfactants suitable for use, if cationic surfactants are used they will make up no more than 1.0% by weight of the composition. If present, they typically make up from 0.001 to 0.7%, and more typically, from 0.001 to 0.5% by weight of the composition.

In an embodiment of the invention, only the surfactants which are sulfate-based; isethionates, taurates and/or glycinates; and betaines and/or sultaines are used in the composition of the invention. In still another embodiment, the total amount of surfactant used in the composition of the present invention (e.g., when optional surfactants are used) should not exceed 20% by weight.

In an embodiment of this invention, the composition of the present invention is substantially free of (less than 0.12% by weight of the composition) polymeric quaternary ammonium compounds (including salts of the same). In another embodiment, the composition of this invention will comprise less than 0.1% by weight polymeric quaternary ammonium compounds. In yet another embodiment, the composition will comprise less than 0.01% by weight polymeric quaternary ammonium compounds. In even another embodiment, the composition is free of polymeric quaternary ammonium compounds (i.e., 0.0%).

Optional skin benefit agents suitable for use in the composition of this invention are limited only to the extent that they are capable of being topically applied, and suitable to dissolve in the composition at the desired pH.

Illustrative examples of the benefit agents suitable to include in the water portion of such compositions are acids, like amino acids, such as arginine, valine or histidine. Additional water-soluble benefit agents suitable for use include vitamin $B_2$, niacinamide (vitamin $B_3$), vitamin $B_6$, vitamin C, mixtures thereof or the like. Water soluble derivatives of such vitamins may also be employed. For instance, vitamin C derivatives such as ascorbyl tetraisopalmitate, magnesium ascorbyl phosphate and ascorbyl glycoside may be used alone or in combination with each other. Other water-soluble benefit agents suitable for use include 4-ethyl resorcinol, extracts like sage, aloe vera, green tea, grapeseed, thyme, chamomile, yarrow, cucumber, liquorice, rosemary extract or mixtures thereof. Water soluble sunscreens like ensulizole may also be used. Total amount of optional water-soluble benefit agents (including mixtures) when present in the composition of the invention may range from 0.0 to 10%, preferably from 0.001 to 8%, and most preferably, from 0.01 to 6% by weight, based on total weight of the composition and including all ranges subsumed therein.

It is also within the scope of the present invention to optionally include oil (i.e., non-water) soluble benefit agents. The only limitation with respect to such oil soluble benefit agents are that the same are suitable to provide a benefit to skin when topically applied. Illustrative examples of the types of oil soluble benefit agents that may optionally be used in the end use composition of this invention include components like stearic acid, vitamins like vitamin A, D, E and K (and their oil soluble derivatives), sunscreens like ethylhexylmethoxycinnamate, bis-ethyl hexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof. Other optional oil soluble benefit agents suitable for use include resorcinols like 4-hexyl resorcinol, 4-phenylethyl resorcinol, 4-cyclopentyl resorcinol, 4-cyclohexyl resorcinol 4-isopropyl resorcinol or a mixture thereof. Also, 5-substituted resorcinois like 4-cyclohexyl-5-methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, stearic acid, palmitic acid, lauric acid, terpineol, thymol mixtures thereof or the like.

In an embodiment of the invention, the optional oil soluble benefit agent used is a retinoic acid precursor. In one embodiment of the invention, the retinoic acid precursor is retinol, retinal, retinyl propionate, retinyl palmitate, retinyl acetate or a mixture thereof. Retinyl propionate, retinyl palmitate and mixtures thereof are typically preferred. Still another retinoic acid precursor suitable for use is hydroxyanasatil retinoate made commercially available under the name Retextra® as supplied by Molecular Design International. The same may be used in a mixture with the oil soluble actives described herein.

When optional (i.e., 0.0 to 1.5% by weight) oil soluble active is used in the oil (including surfactant) phase of the composition of the invention, it typically makes up from 0.001 to 1.3%, and in another embodiment, from 0.05 to 1.0%, and in yet another embodiment, from 0.1 to 0.5% by weight of the total weight of the composition, including all ranges subsumed therein.

While not necessary, it is within the scope of the present invention to optionally include traditional preservatives (in addition to the naturally derived preservatives used in this invention) in the compositions of this invention to protect against the growth of potentially harmful microorganisms. Cosmetic chemists are familiar with appropriate preservatives and routinely choose them to satisfy the preservative challenge test and to provide product stability. Suitable traditional but optional preservatives for use include hydantoin derivatives and propionate salts. Particularly preferred preservatives are iodopropynyl butyl carbamate, phenoxyethanol, 1,2-octanediol, hydroxyacetophenone, ethylhexylglycerine, hexylene glycol, methyl paraben, propyl paraben, imidazolidinyl urea, dimethyl-dimethyl (DMDM) hydantoin and benzyl alcohol and mixtures thereof. Other preservatives suitable for use include chlorophenesin and decylene glycol. The preservatives should be selected having regard for the use of the composition and possible incompatibilities between the preservatives and other ingredients in the composition. These optional preservatives, when used, may be employed in amounts ranging from 0.001% to 2% by weight of the total weight of the composition, including all ranges subsumed therein. In a preferred embodiment of the invention, only the naturally derived preservative comprising benzoic acid and/or a derivative thereof is used without any additional and optional preservatives. It should also be understood that benzoic acid and/or derivatives thereof that are synthetically made are suitable for use in this invention and at the desired pH values, either with or without the naturally derived preservatives.

Thickening agents are optionally suitable for use in the composition of the present invention. Particularly useful are the polysaccharides. Examples include fibers, starches, natural/synthetic gums and cellulosics. Representative of the starches are chemically modified starches such as sodium hydroxypropyl starch phosphate and aluminum starch octenylsuccinate. Tapioca starch is often preferred, as is maltodextrin. Suitable gums include xanthan, sclerotium, pectin, karaya, arabic, agar, guar (including Acacia senegal guar), carrageenan, alginate and combinations thereof. Suitable cellulosics include hydroxypropyl cellulose, hydroxypropyl methylcellulose, ethylcellulose, sodium carboxy methylcellulose (cellulose gum/carboxymethyl cellulose) and cellulose (e.g. cellulose microfibrils, cellulose nanocrystals or microcrystalline cellulose). Sources of cellulose microfibrils include secondary cell wall materials (e.g. wood pulp, cotton), bacterial cellulose, and primary cell wall materials. Preferably the source of primary cell wall material is selected from parenchymal tissue from fruits, roots, bulbs, tubers, seeds, leaves and combination thereof; more preferably is selected from citrus fruit, tomato fruit, peach fruit, pumpkin fruit, kiwi fruit, apple fruit, mango fruit, sugar beet, beet root, turnip, parsnip, maize, oat, wheat, peas and combinations thereof; and even more preferably is selected from citrus fruit, tomato fruit and combinations thereof. A most preferred source of primary cell wall material is parenchymal tissue from citrus fruit. Citrus fibers, such as those made available by Herbacel® as AQ Plus can also be used as source for cellulose microfibrils. The cellulose sources can be surface modified by any of the known methods including those described in Colloidal Polymer Science, Kalia et al., "Nanofibrillated cellulose: surface modification and potential applications" (2014), Vol 292, Pages 5-31.

Synthetic polymers are yet another class of effective thickening agent. This category includes crosslinked polyacrylates such as the Carbomers, acrylate copolymers, acrylates/acrylate ($C_{10}$-$C_{30}$) alkyl acrylate crosspolymers, polyacrylamides such as Sepigel® 305 and taurate copolymers such as Simulgel® EG and Aristoflex® AVC, the copolymers being identified by respective INCI nomenclature as Sodium Acrylate/Sodium Acryloyldimethyl Taurate and Acryloyl DimethyltaurateNinyl Pyrrolidone Copolymer. Another preferred synthetic polymer suitable for thickening is an acrylate-based polymer made commercially available by Seppic and sold under the name Simulgel INS100. Calcium carbonate, salts like sodium chloride, fumed silica, and magnesium-aluminum-silicate may also be used.

The amounts of the thickening agent, when used, may range from 0.001 to 5%, by weight of the composition. Often, thickeners are present at from 0.8 to 3.5% by weight, and preferably, from 1.0 to 3.0% by weight of the composition when petrolatum is included.

Fragrances, fixatives, chelators (like EDTA) salts (like NaCl) and exfoliants may optionally be included in the composition of the present invention. Each of these substances may range from about 0.03 to about 5%, preferably between 0.1 and 3% by weight of the total weight of the composition, including all ranges subsumed therein. To the extent the exfoliants are used, those selected should be of small enough particle size so that they do not impede the performance of any pump and actuator used to dispense composition of this invention.

Conventional humectants, in addition to the polyols previously described, may optionally be employed as additives in the present invention to assist in moisturizing skin when the compositions are topically applied. These are generally polyhydric alcohol type materials. Typical polyhydric alcohols include propylene glycol, dipropylene glycol, polypropylene glycol (e.g., PPG-9), polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. When used, the amount of humectant employed may range anywhere from 0.0 to 35% by weight of the total weight of the composition. Often, humectant makes up from 0.0 to 20%, and preferably, from 0.001 to 15% by weight (most preferably, from 2 to 12% by weight) of the total weight of the composition.

Another optional additive suitable for use includes hemp oil with 2.5 to 25% by weight cannabigerol and/or cannabidiol at from 0.5 to 10 percent by weight. When used, such oil makes up from 0.0001 to 12% by weight of the composition, and preferably, from 0.01 to 5% by weight of the composition, including all ranges subsumed therein.

When making the composition of the present invention, the desired ingredients may be mixed using conventional apparatus under moderate shear and atmospheric conditions, with temperature being from 25 to 90° C.

The packaging for the composition of this invention is limited only to the extent that it is desired for use by consumers and suitable to carry the end use composition if the invention. Typically, the packaging can be a bottle, jar, tube or tub. Preferably, the packaging is durable yet light weight and comprises at least 10% by weight or more of post-consumer resin (PCR) to ensure that its impact on the environment is limited. In a preferred embodiment, the preservative system of the invention is natural and the packaging is all PCR or biodegradable.

The Examples provided are to facilitate an understanding of the invention. They are not intended to limit the scope of the claims.

EXAMPLES

The formulae in these Examples were made by mixing ingredients with moderate shear, under atmospheric conditions and at temperatures from about 50 to 75° C., with the exception that the temperature was reduced to about 45° C. when fragrance was added. The resulting formulae had a pH of 6.5 and a water activity at about 0.96. Each formula made was split and weighed into 5 different aliquots. The 5 different aliquots were then inoculated with a respective organism or organism mix as identified below, resulting in challenged formulations. Inoculum was equal to 1% of the formula weight and at initiation did not alter the character of the formula being challenged. All formulae were thoroughly mixed manually after inoculation to distribute the respective microorganisms uniformly. The challenged formulations were then stored at about 25° C. for the duration of the test. Surfactant was added to base at the amounts indicated.

Antimicrobial Key
Pool 1: *Pseudomonas aeruginosa*+*Burkholderia capacia* (gram negative)
Pool 2: *Klebsiella pneumoniae*+*Enterobacter gergoviae* (gram negative)
3: *Staphylococcus aureus* (Staph. aur.)
4: *Candida albicans* (Yeast)
5: *Aspergillus brasiliensis* (Mold)

Complete Eradication ("CE")—destruction/kill of all microbes present.

Surfactant Key
SLES: Sodium Lauryl Ether Sulfate, 1EO
SLS Sodium Lauryl Sulfate
SLI: Sodium Lauroyl Isethionate
SLMI: Sodium Lauroyl Methyl Isethionate
CAPB: Cocoamidopropyl Betaine
Taurate: Sodium Methyl Lauroyl Taurate Challenged formulations were then sampled for viable microorganisms at 7 days and 14 days. These samples were plated in a petri dish and incubated under conventional conditions appropriate for such test organisms and as identified in the American Type Culture Collection (ATCC), with the middle point of ranges selected when criteria was defined by a range. After incubation, the number of microbial colonies was counted, and the resulting figure was multiplied by the appropriate dilution factor to obtain the number of microorganisms per sample unit.

| Formula Base | |
| --- | --- |
| Ingredient | Weight % Active |
| Water | Balance |
| Thickener | 1.5 |
| Surfactant | As Indicated |
| Chelator | 0.1 |
| Sodium Benzoate | 0.5 |
| Fragrance | 0.9 |
| Petrolatum | 2.0 |
| Stearic Acid | 0.2 |
| Glycerine | 7.0 |
| Sodium Chloride | 0.5 |
| NaOH | 0.1 |

| Formula A: 4.1 wt % SLES; 2.9% SLS; 1.0% wt % SLI; 2.5 wt % CAPB | | |
| --- | --- | --- |
| Antimicrobial | 7 Day | 14 Day |
| Pool 1 | CE | CE |
| Pool 2 | CE | CE |
| Staph. aur. | CE | CE |
| Yeast | CE | CE |
| Mold | 2.70 Log Reduction | 3.09 Log Reduction |

| Formula B: 5.9 wt % SLES; 4.1 wt % SLS; 1.4 wt % SLI; 3.6 CAPB | | |
| --- | --- | --- |
| Antimicrobial | 7 Day | 14 Day |
| Pool 1 | CE | CE |
| Pool 2 | CE | CE |
| Staph. aur. | CE | CE |
| Yeast | CE | CE |
| Mold | 3.87 Leg Reduction | CE |

| Formula C: 1.9 wt % SLES; 1.4 wt % SLS; 0.5 wt % SLMI; 1.2 CAPB | | |
| --- | --- | --- |
| Antimicrobial | 7 Day | 14 Day |
| Pool 1 | CE | CE |
| Pool 2 | CE | CE |
| Staph. aur. | CE | CE |
| Yeast | CE | CE |
| Mold | 2.49 Log Reduction | 2.28 Log Reduction |

| Formula D: 4.6 wt % SLES; 3.4 wt % SLS; 6 wt % SLI; 2.5 wt % CAPB | | |
| --- | --- | --- |
| Antimicrobial | 7 Day | 14 Day |
| Pool 1 | CE | CE |
| Pool 2 | CE | CE |
| Staph. aur. | CE | CE |
| Yeast | CE | CE |
| Mold | 3.34 Log Reduction | CE |

| Formula E: 3.5 wt SLES; 2.5 wt % SLS; 2.0 wt % SLI; 2.5 wt % CAPB | | |
| --- | --- | --- |
| Antimicrobial | 7 Day | 14 Day |
| Pool 1 | CE | CE |
| Pool 2 | CE | CE |
| Staph. aur. | CE | CE |
| Yeast | CE | CE |
| Mold | 3.34 Log Reduction | 3.87 Log Reduction |

| Formula F: 2.3 wt % SLES; 1.7 wt % SLS; 4.0 wt % SLI 2.5 wt % CAPB | | |
| --- | --- | --- |
| Antimicrobial | 7 Day | 14 Day |
| Pool 1 | CE | CE |
| Pool 2 | CE | CE |

-continued

Formula F: 2.3 wt % SLES; 1.7 wt % SLS;
4.0 wt % SLI 2.5 wt % CAPB

| Antimicrobial | 7 Day | 14 Day |
|---|---|---|
| Staph. aur. | CE | CE |
| Yeast | CE | CE |
| Mold | 3.11 Log Reduction | 4.04 Log Reduction |

Formula G: 4.1 wt % SLES; 2.9 wt % SLS;
1.0 wt % SLMI, 2.5 wt % CAPB

| Antimicrobial | 7 Day | 14 Day |
|---|---|---|
| Pool 1 | CE | CE |
| Pool 2 | CE | CE |
| Staph. aur. | CE | CE |
| Yeast | CE | CE |
| Mold | 3.26 Log Reduction | 3.87 Log Reduction |

Formula H: 4.1 wt % SLES, 2.9 wt % SLS,
1 wt % Glycinate, 2.5 wt % CAPB

| Antimicrobial | 7 Day | 14 Day |
|---|---|---|
| Pool 1 | CE | CE |
| Pool 2 | CE | CE |
| Staph. aur. | CE | CE |
| Yeast | CE | CE |
| Mold | 3.04 Log Reduction | 3.44 Log Reduction |

Formula I: 4.1 wt % SLES, 2.9 wt % SLS,
1 wt % Taurate, 2.5% CAPB

| Antimicrobial | 7 Day | 14 Day |
|---|---|---|
| Pool 1 | CE | CE |
| Pool 2 | CE | CE |
| Staph. aur. | CE | CE |
| Yeast | CE | CE |
| Mold | 2.93 Log Reduction | 3.50 Log Reduction |

The formulas made according to this invention were stored for 3 months at 45° C. Surprisingly, after visual assessment by trained panelists, none of the formulas displayed any negative color changes (browning) or phase separation, i.e., syneresis.

Additionally, the formulas made according to this invention, unexpectedly, displayed antimicrobial stability even when they were formulated with sodium benzoate at a pH over the natural pH of skin and with less than 8.0% by weight sulfate-based surfactant. Therefore, the present invention yields stable formulas that can be made with a mild surfactant systems and with preservatives which may be naturally derived.

What is claimed is:

1. An aqueous liquid wash composition comprising:
    (a) a preservative comprising benzoic acid and/or a derivative thereof;
    (b) an anionic surfactant comprising sodium lauryl sulfate, sodium lauryl ether sulfate or mixtures thereof, and sodium lauryl isethionate, sodium methyl lauryl taurate or mixtures thereof;
    (c) a zwitterionic surfactant comprising a cocamidopropyl betaine or a mixture thereof;
    (d) 1 to 9% by weight of a polyol;
    (e) water and;
    (f) 0.01 to 6% by weight of vitamin B2, B3, B6, Vitamin C or a mixture thereof, the composition having a water activity under 1, a pH from 6 to 7 and wherein the weight ratio of zwitterionic surfactant to anionic surfactant is from 1:8 to 1:2, the isethionate is at least 50% by weight of a lauroyl isethionate and the composition comprises less than 7.5% by weight sulfate-based surfactant and further wherein the preservative is 90 to 100% by weight benzoic acid and/or a derivative thereof and the composition has a viscosity from 750 to 22,000 cps, 4 to 15% by weight anionic surfactant, 1 to 5% by weight betaine where the betaine is at least 65% by weight cocamidopropyl betaine, the composition further comprising 40 to 90% by weight water and thickener, the thickener being present at 0.8 to 3.5% by weight when the aqueous liquid wash composition comprises petrolatum.

2. The composition according to claim 1 wherein the alkyl sulfate comprises sodium lauryl sulfate and the alkyl ether sulfate is sodium lauryl ether sulfate and the zwitterionic surfactant is a betaine making up from 1.5 to 3.5% by weight of the composition and further wherein isethionate is present and makes up from 0.4 to 4% by weight of the composition and the polyol is at least 50% by weight glycerol making up from 2 to 8% by weight of the composition.

3. The composition according to claim 1 wherein the alkyl ether sulfate comprises a mixture of surfactants with 1, 2 and 3 ethylene oxide units and 10 to 90% by weight of the anionic surfactant is sodium lauryl ether sulfate.

4. The composition according to claim 2 wherein the zwitterionic surfactant which is a betaine is cocoamidopropyl betaine.

5. The composition according to claim 1 wherein the anionic surfactant which is a sulfate makes up less than 7.2% by weight of the composition and the anionic surfactant which is an isethionate is from 0.5 to 2% by weight of the composition and further wherein the anionic surfactant which is a sulfate is at least 40% by weight sodium lauryl ether sulfate, the composition further comprising grapeseed oil, jojoba oil, sunflower oil, shea butter, or a mixture thereof.

6. The composition according to claim 1 wherein the weight ratio of zwitterionic surfactant to anionic surfactant is from 1:6 to 1:2 and the composition has a pH from 6.2 to 6.8 and a viscosity from 2,000 to 18,000 cps.

7. The composition according to claim 1 wherein the weight ratio of zwitterionic surfactant to anionic surfactant is from 1:4 to 1:3, the composition is isotropic and comprises sodium chloride.

8. The composition according to claim 1 wherein the composition comprises from 45 to 85% by weight water and 1.5 to 3.5% by weight betaine and at least 4% by weight sulfate-based surfactant.

9. The composition according to claim 1 wherein the preservative comprises synthetically made sodium, potassium or amino benzoate.

10. The composition according to claim 1 wherein the preservative comprises naturally derived sodium, potassium or amino benzoate.

11. The composition according to claim 1 wherein the composition comprises terpineol, thymol or both.

12. The composition according to claim 1 wherein the composition displays an antimicrobial log kill of 2 after 14 days.

13. The composition according to claim 1 wherein the composition further comprises from 0.01 to 6% by weight petrolatum.

14. The composition according to claim 1 wherein the composition further comprises 12-hydroxystearic acid or a mixture thereof.

15. The composition according to claim 1 wherein the thickener is from 0.0001 to 5% gum, starch, cellulose or crosslinked polyacrylate.

16. The composition according to claim 1 wherein the preservative is 100% by weight benzoic acid and/or a derivative thereof and the composition further comprises chamomile, rosemary extract or both.

17. The composition according to claim 1 wherein the composition comprises glycerol as polyol and palmitic acid, and stearic acid, 12 hydroxystearic acid or both, and preservative makes up from 0.3 to 1.5% by weight of the composition.

18. The composition according to claim 16 wherein the preservative makes up from 0.4 to 0.65% by weight of the composition.

19. The composition according to claim 1 wherein the composition is packaged in packaging comprising post-consumer resin.

20. A method for treating skin comprising the steps of:
a) contacting skin in need of washing with the composition of claim 1; and
b) rinsing the composition off the skin with water.

21. The composition according to claim 1 wherein the preservative is natural, synthetic or a mixture of natural and synthetic preservatives.

22. The composition according to claim 1 wherein the composition further comprises 1,2-octanediol.

23. The composition according to claim 1 wherein the composition further comprises an acyl sarcosinate.

24. The composition according to claim 1 wherein the composition comprises Vitamin C.

25. The composition according to claim 1 wherein the composition further comprises 0.001 to 15% by weight propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol or a mixture thereof.

* * * * *

UNITED STATES PATENT AND TRADEMARK OFFICE
CERTIFICATE OF CORRECTION

PATENT NO. : 12,076,427 B2
APPLICATION NO. : 17/881901
DATED : September 3, 2024
INVENTOR(S) : Kimberly Day et al.

Page 1 of 1

It is certified that error appears in the above-identified patent and that said Letters Patent is hereby corrected as shown below:

In the Claims

Column 15, Line 66, In Claim 1, delete "sodium lauryl isethionate, sodium methyl lauryl" and insert --sodium lauroyl isethionate, sodium methyl lauroyl-- therefor.

Signed and Sealed this
Eighth Day of October, 2024

Katherine Kelly Vidal
*Director of the United States Patent and Trademark Office*